United States Patent [19]
Tam et al.

[11] Patent Number: 6,086,913
[45] Date of Patent: Jul. 11, 2000

[54] LIPOSOMAL DELIVERY OF AAV VECTORS

[75] Inventors: Patrick Tam; Arcadio Chonn, both of Vancouver, Canada

[73] Assignee: University of British Columbia, Burnaby, Canada

[21] Appl. No.: 08/736,163

[22] Filed: Oct. 25, 1996

Related U.S. Application Data

[60] Provisional application No. 60/007,193, Nov. 1, 1995.

[51] Int. Cl.$^7$ .......................... A61K 9/127; A61K 9/133; C12N 15/86
[52] U.S. Cl. .................. 424/450; 435/320.1; 435/235.1; 435/69.1; 435/458; 536/23.2; 536/23.7
[58] Field of Search ................................. 435/69.1, 172.1, 435/172.3, 235.1, 320.1, 458; 424/450; 536/23.2, 23.7

[56] References Cited

U.S. PATENT DOCUMENTS

| | | | |
|---|---|---|---|
| 4,797,368 | 1/1989 | Carter et al. | 435/320.1 |
| 5,139,941 | 8/1992 | Muzyczka et al. | 435/456 |
| 5,264,618 | 11/1993 | Felgner et al. | 560/224 |
| 5,354,678 | 10/1994 | Lebkowski et al. | 435/463 |
| 5,436,146 | 7/1995 | Shenk et al. | 435/457 |
| 5,587,308 | 12/1996 | Carter et al. | 435/371 |

FOREIGN PATENT DOCUMENTS

| | | |
|---|---|---|
| WO 91/18088 | 11/1991 | WIPO . |
| WO 95/06743 | 3/1995 | WIPO . |
| WO 95/07995 | 3/1995 | WIPO . |
| WO 95/13365 | 5/1995 | WIPO . |
| WO 95/13392 | 5/1995 | WIPO . |

OTHER PUBLICATIONS

Baudonis Wendy et al., "Genomic Targeting With Purified Cre Recombinase," *Nucleic Acids Research*, 1993, vol. 21, No. 9, pp. 2025–2029.

Holt Cydne L. et al., "A Novel Phage λ Replacement Cre–Lox Vector That Has Automatic Subcloning Capabilities," *Gene*, 1993, vol. 133, pp. 95–97.

Kotin Robert M. et al., "Site–Specific Integration By Adeno–Associated Virus," *Proc. Natl. Acad. Sci.*, Biochemistry, Mar. 1990, vol. 87, pp. 2211–2215.

Kotin Robert M., "Prospects For The Use of Adeno–Associated Virus As A Vector For Human Gene Therapy," *Human Gene Therapy*, 1994, vol. 5, pp. 793–801.

Lebkowski Jane s., "Genetic Modification of Unstimulated Primary Tumor CD+ And Antigen Presenting Cells Using Liposome AAV Plasmid Complexes: Clinical Applications," S5 #7, p. 35.

Ma Yuliang et al., "Comparative Analysis of the Structure and Function of Adenovirus Virus–Associated RNAs," *Journal of Virology*, Nov. 1993, vol. 67, No. 11, pp. 6005–6617.

Muzyczka N., "Use of Adeno–Associated Virus as a General Transduction Vector for Mammalian Cells," *Microbiology and Immunology*, 1992, vol. 158, pp. 98–127.

Nahreini Piruz et al., "Cloning and Integration of DNA Fragments in Human Cells via the Inverted Terminal Repeats of the Adeno–Associated Virus 2 Genome," *Gene*, 1992, vol. 119, pp. 265–272.

Philip Ramila et al., "Efficient and Sustained Gene Expression in Primary T Lymphocytes and Primary and Cultured Tumor Cells Mediated by Adeno–Associated Virus Plasmid DNA Complexed to Cationic Liposomes," *Molecular and Cellular Biology*, Apr. 1994, vol. 14, No. 4, pp. 2411–2418.

Rolling Fabienne et al., "AAV as a Viral Vector for Human Gene Therapy, Generation of Recombinant Virus," *Molecular Biotechnology*, 1995, vol. 3, pp. 9–15.

Samulski Richard Jude et al., "Helper–Free Stocks of Recombinant Adeno–Associated Viruses: Normal Integration Does Not Require Viral Gene Expression," *Journal of Virology*, Sep. 1989, vol. 63, No. 9, pp. 3822–3828.

Samulski Richard Jude et al., "Targeted Integration of Adeno–Associated Virus (AAV) Into Human Chromosone 19," *The EMBO Journal*, 1991, vol. 10, No. 12, pp. 3941–3950.

Smith Andrew J. H. et al., "A Site–Directed Chromosomal Translocation Induced in Embryonic Stem Cells by Cre–Loxp Recombination," *Nature Genetics*, Apr. 1995, vol. 9, pp. 376–385.

Sauer Brian, "Manipulation of Transgenes by Site–Specific Recombination: Use of Cre Recombinase," *Methods in Enzymology*, 1993, vol. 225, pp. 890–900.

Walsh Christopher E. et al., "Regulated High Level Expression of a Human γ— Globin Gene Introduced Into Erythroid Cells by an Adeno–Associated Virus Vector," *Proc. Natl. Acad. Sci.*, Medical Sciences, Aug. 1992, vol 89, pp. 7257–7261.

Walsh Christopher E. et al., "Gene Therapy for Human Hemoglobinopathies," *Gene Therapy for Human Hemoglobiopathies*, 1993, vol. 204, pp. 289–300.

Walsh Christopher E. et al., Phenotypic Correction of Fanconi Anemia in Human Hematopietic Cells With a Recombinant Adeno–Associated Virus Vector, *The Journal of Clinical Investigation, Inc.*, Oct. 1994, vol. 94, pp. 1440–1448.

Wu Ping et al., "Sendai Virosomal Infusion of an Adeno–Associated Virus–Derived Construct Containing Neuropeptide Y into Primary Rat Brain Cultures," *Neuroscience Letters*, 1995, vol. 190, pp. 73–76.

*Primary Examiner*—David Guzo
*Attorney, Agent, or Firm*—Townsend and Townsend and Crew LLP

[57] ABSTRACT

The invention provides compositions and methods for introducing a nucleic acid fragment into the genome of a cell. Suitable compositions comprise an expression vector having first and second inverted repeated sequences from an adeno associated virus, a rep gene from an adeno associated virus and the nucleic acid fragment. The expression vector is complexed with lipids.

13 Claims, 5 Drawing Sheets

LIPOSOMAL DELIVERY OF AAV VECTORS

CROSS REFERENCE TO RELATED APPLICATIONS

This application is a continuation of provisional application Ser. No. 60/007,193, filed Nov. 1, 1995, which is incorporated herein by reference in its entirely for all purposes.

BACKGROUND OF THE INVENTION

There have been several approaches to gene therapy, each of which has inherent drawbacks. For example, recombinant retroviral vectors have been used to integrate a gene of interest into a target cell genome. However, retroviruses integrate efficiently only into replicating calls and they are difficult to concentrate and purify. Further, there is concern that retroviruses are carcinogenic.

Several DNA viruses, such as adenovirus, have also been engineered to serve as vectors for gene transfer. But adenoviruses can carry only a limited insert and are often restricted in the range of cells they infect. Moreover, adenoviruses fail to integrate their inserts into the host genome leading to only transient expression. Host immunity also pose problems for repeated administration. A further difficulty is that recipient cells generally express viral proteins in addition to the therapeutic gene, and these viral proteins cause immune responses and subsequent inflammation in the recipient organ.

Some of these drawbacks are overcome by utilizing adenoassociated virus (AAV), which is a single-stranded DNA parvovirus. AAV is a defective virus that productively infects only cells in which certain functions are provided by a co-infecting helper virus such as adenovirus and herpesvirus. Infection of cells with AAV in the absence of helper functions results in integration of AAV into the host call genome without replication. The AAV genome has two copies of a 145-nucleotide-long ITR (inverted terminal repeat), one at each end (Srivastava et al., *J. Virol.*, 45, 555–564 (1983)). The ITR sequences provide an origin of replication and also mediate integration and excision of the AAV genome from the cell genome.

The sequence between the ITRs of about 4470 nucleotides contains two open-reading frames for rep and cap genes (Hermonat et al., *Virology* 51, 329–339 (1984)). The cap gene encodes capsid proteins. The rep gene encodes proteins known to be required for replication. A possible additional function of rep proteins, integration of AAV DNA into the host genome, remains controversial. There is some evidence that rep⁻ vectors show reduced preference for site-specific integration into chromosome 19. However, it has been reported that the overall integration frequency of rep⁻ vectors is higher than that of comparable rep⁺ vectors. McLaughlin et al., *J. Virol.* 62, 1963–1973 (1988).

AAV is nontransforming and not associated with any disease (Ostrove et al., *Virology* 113, 521 (1981); Cukor et al., in *The Parvoviruses* (ed. Berns, Plenum, N.Y., 1984)). Further, AAV virions are resistant to physical treatments, such as sonication and heat inactivation not tolerated by other viruses during purification (Samulski et al., *J. Virol.* 63, 3822–3828 (1989)). Like retroviruses, AAV integrates into the host cell genome upon infection (Kotin et al., *Proc. Natl. Acad. Sci. USA* 87, 2211–2215 (1990); Samulski et al., *EMBO J.* 10, 3941–3950 (1991)). However, unlike retroviruses, AAV preferentially integrates at a specific chromosomal site (19q13.3) (AAVI). At this site, AAV does not cause any significant alteration in the growth properties or morphological characteristics of human cells. Furthermore, integration of AAV into the cellular genome can occur in nonproliferating cells. (Lebkowski et al., *Mol. Cell. Biol.* 8, 3988–3996 (1988)).

Nevertheless, existing methods of using AAV for gene transfer have several drawbacks. A major problem limiting the practical use of recombinant AAV is that AAV production methods are inefficient and laborious (Lebkowski et al., 1988, supra; Samulski et al., 1989, supra; Muzyczka, *Curr. Top. Microbiol. Immunol.* 158, 97–129 (1992)). In recombinant AAV, all protein coding sequence (such as cap, and rep) are usually replaced by the exogenous gene of interest. Recombinant AAV is replicated by co-transfecting a cell bearing the AAV vector carrying the gene of interest, together with a helper AAV plasmid that expresses all of the essential AAV genes, into adenovirus-infected cells, which supply additional helper functions necessary for AAV replication and the production of new viral particles. Using this approach, it is difficult to obtain the high yields of packaged viral genomes that are required for use in gene therapy. Further, the preparation of recombinant AAV may be contaminated with wildtype AAV from the helper plasmid or infectious virions of the helper virus, such as herpes or adenovirus. An additional drawback from packaging AAV genomes before introduction of cells is that the maximum size of an insert compatible with packaging is limited to about 5 kb.

Some of the disadvantages stemming from the use of viral vectors are avoided by transfecting a DNA fragment into cells nonbiologically, for example, by lipofection, chemical transformation or electroporation. In this approach, ample amounts of pure DNA can be prepared for transfections, and much larger fragments can be accommodated. To-date, however, such approaches have been limited to cells that can be temporarily removed from the body. Furthermore, the efficiency of gene integration has been very low, about one integration event per 1,000 to 100,000 cells, and expression of transfected genes has been limited to days in proliferating cells or weeks in nonproliferating cells. Without integration, expression of the transfected gene may be limited to several days in proliferating cells or several weeks in nonproliferating cells due to the degradation of the unintegrated DNA.

A further method has been proposed in which a recombinant vector containing AAV ITR sequences but lacking all other AAV sequences is surrounded by cationic lipids and introduced into a cell by lipofection. Philip et al., WO 95/07995. However, this method does not result in efficient integration. Lebkowski et al., *Society Francaise de Microbiologie, VIth Parvovirus Workshop*, Abstract S5 #7.

Accordingly, there is a need for improved AAV cloning vectors and methods of transferring the same into recipient cells. The present invention fulfills this and other needs.

SUMMARY OF THE INVENTION

The invention provides compositions and methods for introducing a nucleic acid fragment into the genome of a cell. Such a composition comprises an expression vector comprising first and second inverted repeated sequences from an adeno associated virus, a rep gene from an adeno associated virus and the nucleic acid fragment. The expression vector is complexed with lipids. Optionally, the vector further comprises at least one gene encoded by adenovirus DNA segments E1–E4, and some vectors include each of these segments. Optionally, the vector includes a loxP site. Often, the nucleic acid fragment encodes a protein coding sequence in operable linkage to a promoter. Alternatively, the fragment can encode an antisense transcript.

The invention further provides methods of modifying the phenotype of cells, comprising contacting the cells with compositions as described above. Often, the cells to be modified have a mutant gene associated with a defective expression product. The DNA fragment encodes a functional expression product of the gene and the gene integrates into the genome of the cells and is expressed. Optionally, the composition further comprises a pharmaceutical excipient. In some methods, the cells are from a patient suffering from a disease resulting from the mutant form of the gene, and the method further comprising reintroducing the cells into the patient. In some methods, the recipient cells are incapable of replication. In some methods, the nucleic acid fragment integrates into about 5% of the recipient cells. In some methods, the cells are contacted with the composition in vivo in a patient.

DEFINITIONS

Figure 1:
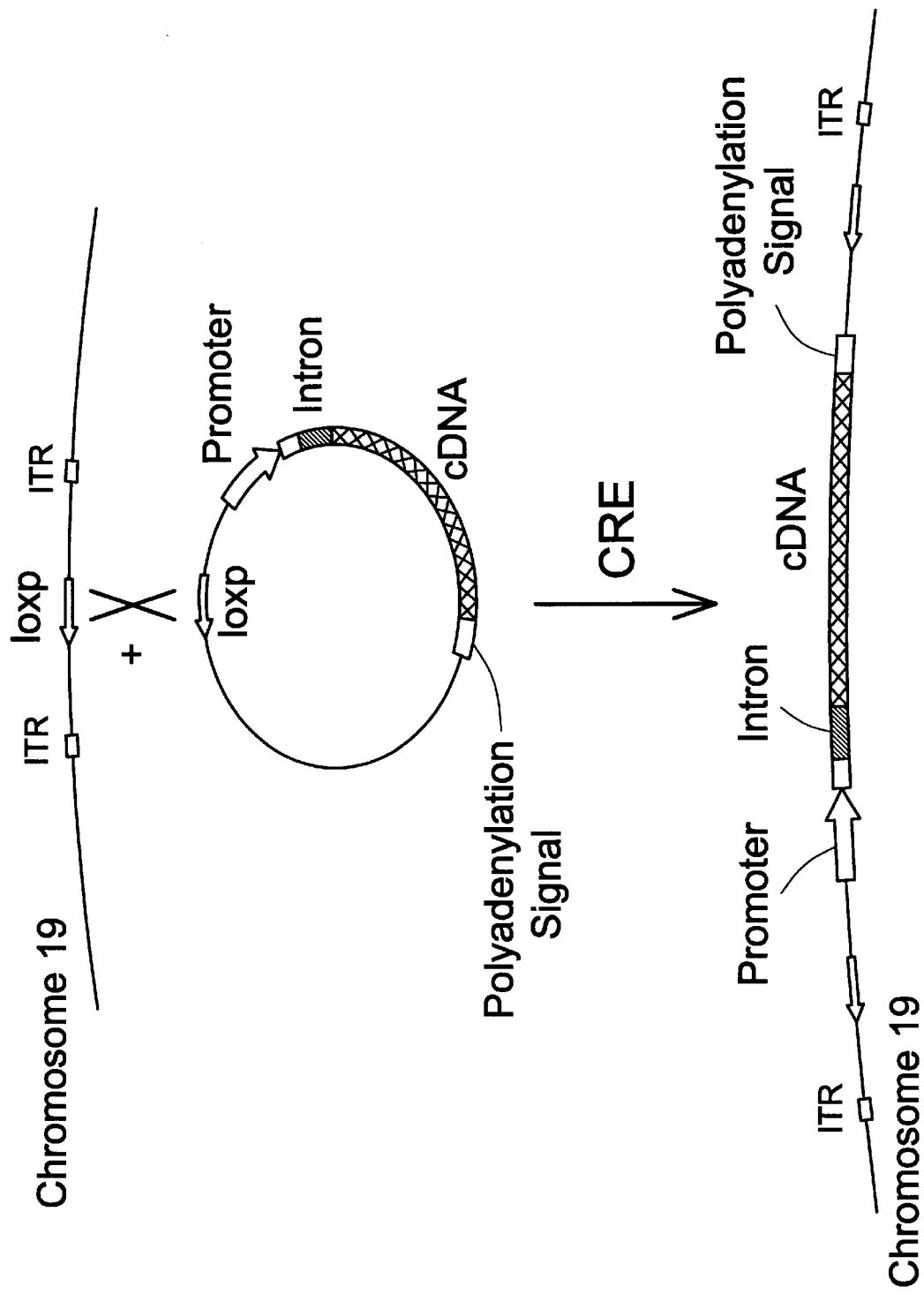
FIG. 1: LoxP-mediated recombination of a vector bearing a coding sequence of interest with a recombinant adenoassociated virus vector integrated into chromosome 19.

A DNA segment is operably linked when placed into a functional relationship with another DNA segment. For example, a promoter or enhancer is operably linked to a coding sequence if it stimulates the transcription of the sequence. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof.

A mutant allele of a gene is associated with a genetic disease, in that an addition, deletion or substitution of one or more nucleotides in the gene (including complete deletion of the gene) relative to the wildtype allele causes the disease phenotype in at least some individuals bearing the mutant allele. The phenotype may result from a nucleotide change in the gene (addition, deletion or substitution) affecting expression of the gene by altering the kinetics of expression or the nature of the resulting expression product.

DESCRIPTION OF THE PREFERRED EMBODIMENT

The invention provides AAV vectors comprising ITRs, rep and an exogenous DNA fragment, compositions in which the vectors are complexed with lipids, and methods of introducing the compositions into host cells. The methods may be practiced in vivo or in vitro.

I. AAV Genetics

The AAV genome is a linear single-stranded DNA molecule having a molecular weight of about 1.5 MDa and a length of about 4680 nucleotides. Both sense and antisense strands are packaged into particles with equal frequency but each particle has only one single-stranded DNA molecule. Both strands are infectious. Replication occurs by conversion of the parental infecting single strand to a duplex form and subsequent amplification of a large pool of duplex molecules from which progeny single strands are displaced and packaged into capsids. Duplex or single-strand copies of AAV genomes inserted into bacterial plasmids or phagemids are also infectious.

The sequence of the most common type of AAV, termed AAV-2, has been determined previously (Genbank locus AA2CG) and exhibits the hallmark characteristics of parvoviruses. Minor corrections in the Genbank sequence are noted in Muzyczka, supra. The termini of AAV-2 contain 145 bp inverted repeats (ITRs) bracketing the internal coding portion of the genome and three promoters. (Laughlin et al., *Proc. Natl. Acad. Sci* (*USA*) 76, 5567–5571 (1979)). The rep gene is located in the 5' half of the genome and the capsid gene is located in the 3' half of the genome. The rep gene is expressed from two promoters, p5 and p19. Transcription from p5 yields an unspliced 4.2 kb mRNA which encodes a protein, Rep78, and a spliced 3.9 kb MRNA which encodes a protein, Rep68. Transcription from p19 yields an unspliced mRNA which encodes Rep52 and a spliced 3.3 kb mRNA which encodes Rep40. Thus, the four Rep proteins all have a common internal region sequence but differ with respect to their amino and carboxyl terminal regions. Only Rep78 and Rep68 are required for AAV duplex DNA replication, but Rep52 and Rep40 also appear to be needed for single-stranded DNA accumulation.

Capsid proteins VP1, VP2, and VP3 share a common overlapping sequence but differ in that Vp1 and VP2 contain additional amino terminal sequence. All three are coded from the same cap gene reading frame expressed from a spliced 2.3 kb mRNA transcribed from the p40 promoter. VP2 and VP3 are generated from the same mRNA by use of alternate initiation codons. VPI is coded from a minor mRNA using from a donor site 30 nucleotides upstream from the donor site of the major MRNA that encodes VP2 and VP3.

General reviews of AAV include Carter, 1989, *Handbook of Parvoviruses*, Vol. I (Raven Press, New York), pp. 169–228; Kotor, *Human Gene Therapy* 5, 793–801 (1994).

II. Components of Recombinant AAV Vectors

AAV vectors of the present invention are constructed by inserting a DNA fragment of interest into the vector, usually substituting for some and preferably, all of the cap coding sequence. The ITR sequences (or subsequences thereof sufficient to mediate integration) are retained. Also retained is the rep gene or a functional fragment thereof sufficient to significantly stimulate integration relative to a rep⁻ vector. The relative positioning of the rep gene relative to the ITRs is not critical. In some vectors, the the ITR sequences surround the rep sequence in similar arrangement to that in a natural AAV virus. In other vectors, the rep gene is outside the ITR sequences. The rep gene can also be expressed in trans to the ITR sequences on a different vector. The rep gene usually includes both of the endogenous promoter sequences from which rep proteins are expressed. However, rep can also be operably linked to other promoters, such as SV40, CMV or β-gal.

The DNA fragment of interest can be cDNA, genomic, minigene (genomic with one or more introns omitted), synthetic or a hybrid of any of these. Genomic sequences often lead to higher levels of expression. The fragment often encodes a protein. The nature of the protein depends on the intended use. In some gene therapy applications, the protein is a functional expression product such as can compensate for the defective expression product of a mutant gene. For example, the DNA fragment can encode the coding sequence of a wildtype form of the gene. Alternatively, the expression product can be an antisense sequence exhibiting complementarity to the genome of a microorganism. In some applications, more than one fragment of interest is inserted, and the vector is thus capable of expressing multiple proteins.

If the DNA fragment of interest is a protein-coding sequence, the sequence is operably linked to a promoter and preferably an enhancer. The promoter and enhancer should be functional in the cell or tissue type in which it is desired that expression be obtained. Some promoter and enhancers are relatively nontissue specific (e.g., regulatory sequences derived from immunoglobulin genes, SV40, adenovirus, bovine papilloma virus, cytomegalovirus). Others regulatory sequences promote expression more effectively in a specific tissue type. For example, casein regulatory sequences promote expression in mammary tissue, albumin regulatory sequences in liver, α-actin sequences in muscle and protamine sequences in spermatids.

DNA fragments encoding proteins are also preferably operably linked at the 3' end to a polyA encoding sequence. This sequence can be a natural AAV polyA sequence or an exogenous polyA sequence, such as the SV40 large T antigen polyA sequence.

The size of the insert has no absolute upper limit and can range from about 8 bp (e.g., an antisense sequence) to over 100 kb (e.g., a genomic sequences). However, transfection frequencies may decline toward the high end of this range. Thus, insert sizes of at least 100, 500, 5000, 6000, or 10,000 but less than 50,000 bp are common.

Some vectors include an additional DNA segment encoding a selection marker, which is usually operably linked to a promoter. Suitable selection markers include neo, hprt, hyg, and gpt. Selection markers expressed in a recipient cell grown on appropriate media confer a survival advantage on the cell relative to cells lacking the marker. Inclusion of a selection marker is particularly useful when the intended use of the vector is transfection of cells in vitro. The selection marker allows selection of cells that have integrated the vector. Some vectors include only part of the complete sequence encoding a selection markers. Such sequences can recombine with a complementing partial sequence in the genome of recipient cells to generate an intact coding sequence capable of expressing a functional selection marker.

Some vectors include an additional fragment encoding one or more proteins encoded by the genome of helper viruses, such as Adenovirus 5. The adenoviral genome encodes at least 30 mRNA species and is organized into several early and late transcriptional regions, each of which plays a specific role in the viral life cycle. There are four early regions (E1–E4) and one major late region with five principal coding units (L1–L5). See generally Field, *Virology* (Chanock et al. eds. 2d ed. Raven N.Y. 1990) (incorporated by reference in its entirety for all purposes). In addition, there are several minor intermediate and/or late regions. The E1 region is active immediately upon entry of the viral genome into the host cell nucleus and encodes proteins that regulate all the other early functions. The E2 region encodes proteins involved in viral DNA replication such as a DNA-binding protein which appears to be involved in transcriptional control, and the DNA polymerase. E3 encodes polypeptides involved in viral mechanisms which interact with the host cell and diminish recognition of infected cells. For example, an E3-encoded 19 kDa glycoprotein associates with the class I antigens of the major histocompatibility complex and inhibits their transport to the surface of infected cells. The E4-encoded proteins function in the shut-down of host gene expression in favor of that of the virus. In addition, E4 proteins serve to upregulate transcription from other regions. The major late region codes for most of the polypeptides that make up the capsid. These adenoviral proteins play various roles in the earlier steps of AAV infection, such as adsorption, uncoating and second strand synthesis. For instance, the open reading frame 6 (ORF6) of the E4 region is necessary in an early step in the AAV lifecycle. They may also play a role in enhancing gene expression from the AAV vector. One or more of these segments encoding one or more proteins of adenovirus are included in some recombinant AAV vectors or in the genome of a recipient cells to increase the efficiency of transduction and integration. Protein-coding sequences within these segments are linked to a promoter, which can be their natural adenovirus promoter or an exogenous promoter. The protein-coding sequences, therefore, provide helper functions that complement the AAV recombinase protein in the absence of helper virus.

Figure 2:
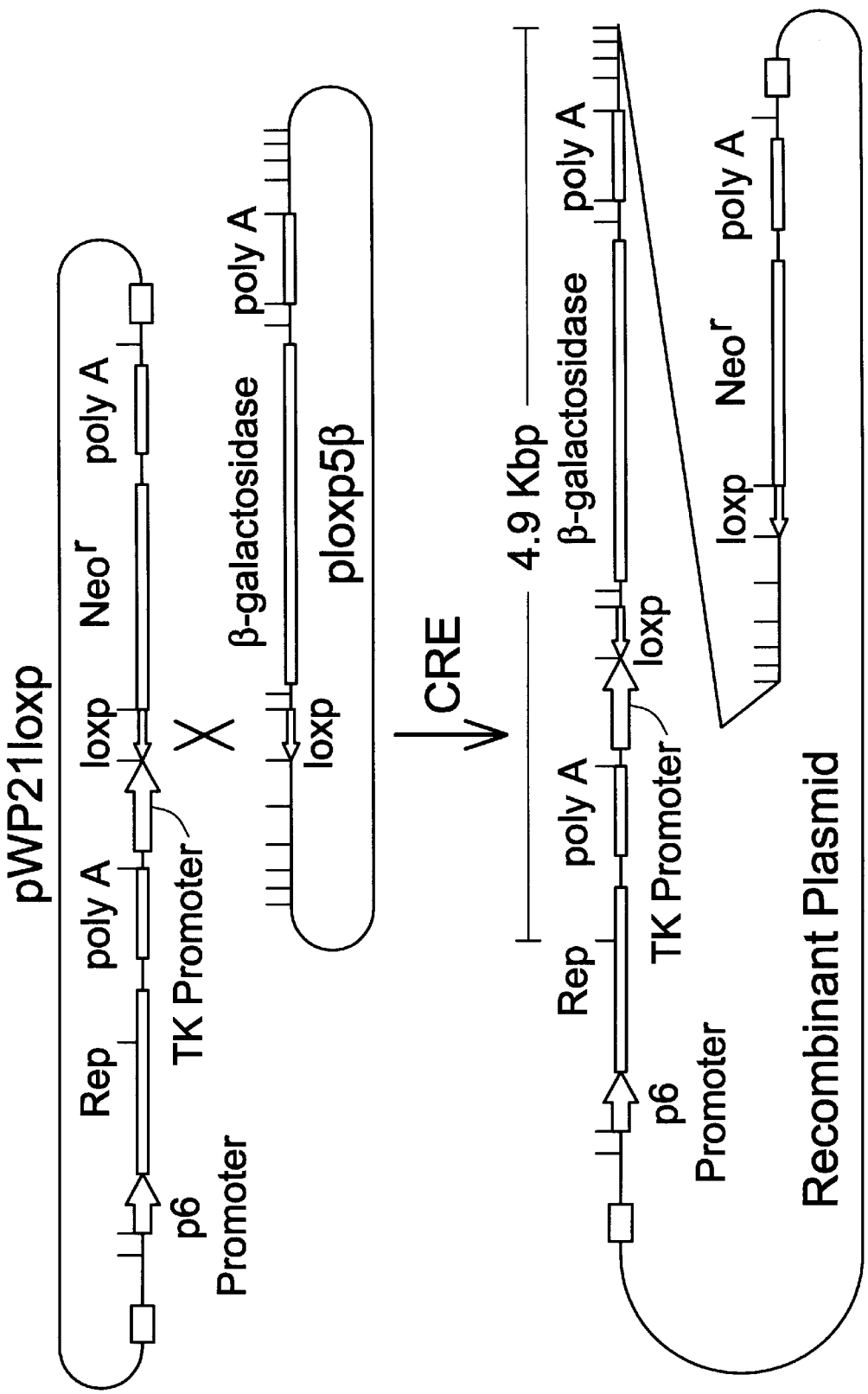
FIG. 2: Rearrangement of DNA fragments following LoxP-mediated recombination.

Other vectors include sequences corresponding to a loxP site. LoxP refers to a 34 bp sequence naturally occurring in bacteriophage P1 and whose natural occurrence in the mammalian genome is highly unlikely. The dyad-symmetric loxP site is composed of two 13 bp inverted repeats, separated by a 8 bp spacer region (Sternberg & Hamilton, *J. Molec. Biol.* 150, 467–486 (1981)). The AAV vectors containing a loxP site flanked by ITRs can be used to integrate a loxP site into the genome of target cells (human, monkey, hamster) in a preferential site on chromosome 19. The unique loxP sequence can then be utilized as a target sequence for the reaction catalyzed by the Cre recombinase enzyme from bacteriophage P1. In a second reaction the presence of bacteriophage P1 Cre recombinase and a targeting plasmid vector (consisting of a loxP sequence, a mammalian promoter, the coding sequence of a gene, polyadenylation sequence, or other regulatory elements such as locus control regions, or introns, or translational enhancer elements) results in the site-specific integration of the targeting plasmid vector into the chromosomal loxP site (see Baubonis & Sauer, *Nucleic Acids Research* 21,2025–2029 (1993)). A general scheme for introducing a vector into a chromosome by loxP mediated recombination is shown in FIG. 1. The specific arrangements of DNA following loxP mediated recombination of vector pWP21loxP with a vector termed ploxp5β harboring an exemplary coding sequence are shown in FIG. 2. The Cre recombinase protein can be introduced directly into the target cell by lipofection, or can be encoded by the AAV vector (operably linked to a promoter), or can be co-transfected on a separate construct with the targeting vector, or can be previously integrated into the genome of the target cell.

The integrated targeting plasmid vector can be excised from the integrated site at a subsequent time. This is accomplished by delivering either purified Cre recombinase protein or a vector containing the coding region of Cre recombinase operably linked to a promoter. Cre recombinase efficiently catalyzes the excision of nucleic acids flanked by loxP sites. This is advantageous for instance if the integrated targeting vector becomes mutated, or if the promoter becomes inoperable resulting in loss or reduction in levels of gene expression, or if an improved gene is discovered, or if the regulatory sequences do not result in optimum levels of gene expression.

The AAV vectors of the invention usually contain a procaryotic origin of replication. Thus, the vectors can be propagated in *E. coli* by standard techniques to generate large amounts of DNA.

In vectors, harboring multiple structural genes, usually each gene is linked to its own promoter and other regulatory sequences, and the relative order of genes in the vector is not critical.

III. Lipid Transfection System

The AAV vectors discussed above are complexed with lipids before contacting with host cells. The resulting complexes should be sufficiently small and stable in circulation to distribute from local injection sites when given intravenously, capable of carrying a large amount of DNA per particle to enable transfection of all sizes of genes and reduce the volume of injection, homogenous, reproducible, and protective of DNA from extracellular degradation and capable of transfecting target cells in such a way that the DNA is not digested intracellularly. In some methods, Cre enzyme is also complexed with lipids to allow its introduction into recipient cells.

Preferred lipids for complexing with AAV vectors and methods for associating the two components are described by commonly owned copending U.S. Ser. No. 08/485,458, filed Jun. 7, 1995, now U.S. Pat. No. 5,705,385, and U.S. Ser. No. 08/484,282, filed Jun. 7, 1995, now U.S. Pat. No. 5,981,501 (incorporated by reference in their entirety for all purposes). Preferred cationic lipids include DODAC, DOTMA, DDAB, DOTAP, DC-Chol and DMRIE. These lipids and related analogs, which are also useful in the present invention, have been described in co-pending U.S. Ser. No. 08/316,399, now abandoned; U.S. Pat. Nos. 5,208, 036, 5,264,618, 5,279,833 and 5,283,185, Additionally, a number of commercial and other preparations of cationic lipids are available and can be used in the present invention. These include, for example, "LIPOFECTIN" (commercially available cationic liposomes comprising DOTMA and DOPE, from GIBCO/BRL, Grand Island, N.Y., USA); "LIPOFECTAMINE" (commercially available cationic liposomes comprising DOSPA and DOPE, from GIBCO/BRL); and "TRANSFECTAM" (commercially available cationic liposomes comprising DOGS from Promega Corp., Madison, Wis., USA). Virosomes, as described in commonly owned U.S. Ser. No. 08/251,469, filed May 31, 1994, now abandoned and U.S. Ser. No. 08/454,641, filed May 31, 1995, now abandoned , (incorporated by reference in their entirety for all purposes), can also be used.

In some methods, an initial solution of coated AAV vector-lipid complexes is formed by combining the vector with the cationic lipids in a detergent solution. The detergent solution is preferably an aqueous solution of a neutral detergent having a critical micelle concentration of 15–300 mM, more preferably 20–50 mM. Examples of suitable detergents include, for example, N, N'-((octanoylimino)-bis-(trimethylene))-bis-(D-gluconamide) (BIGCHAP); BRIJ 35; Deoxy-BIGCHAP; dodecylpoly(ethylene glycol) ether; Tween 20; Tween 40; Tween 60; Tween 80; Tween 85; Mega 8; Mega 9; "Zwittergent" 3–08; "Zwittergent" 3–10; Triton X-405; hexyl-, heptyl-, octyl- and nonyl-β-D-glucopyranoside; and heptylthioglucopyranoside; with octyl β-D-glucopyranoside being the most preferred. The concentration of detergent in the detergent solution is typically about 100 mM to about 2 M, preferably from about 200 mM to about 1.5 M.

The cationic lipids and vector are typically combined to produce a charge ratio (+/−) of about 1:1 to about 20:1, preferably in a ratio of about 1:1 to about 12:1, and more preferably in a ratio of 1.5:1. Additionally, the overall concentration of plasmid in solution is typically from about 25 μg/ml to about 1 mg/ml, preferably from about 25 μg/ml to about 200 μg/ml, and more preferably from about 50 μg/ml to about 100 μg/ml. The combination of vector and cationic lipids in detergent solution is kept, typically at room temperature, for a period of time which is sufficient for the coated complexes to form. Alternatively, the plasmids and cationic lipids can be combined in the detergent solution and warmed to up to about 37° C.

The detergent solution of the coated plasmid-lipid complexes is then contacted with noncationic lipids to provide a detergent solution of plasmid-lipid complexes and noncationic lipids. Noncationic lipids useful in this step include, diacylphosphatidylcholine, diacylphosphatidylethanolamine, ceramide, sphingomyelin, cephalin, cardiolipin, and cerebrosides. In preferred embodiments, the noncationic lipids are diacylphosphatidylcholine, diacylphosphatidylethanolamine, ceramide or sphingomyelin. The acyl groups in these lipids are preferably acyl groups derived from fatty acids having $C_{10}$–$C_{24}$ carbon chains. More preferably the acyl groups are lauroyl, myristoyl, palmitoyl, stearoyl or oleoyl. In particularly preferred embodiments, the noncationic lipid is 1,2-sn-dioleoylphosphatidylethanolamine (DOPE), palmitoyl oleoyl phosphatidylcholine (POPC) or egg phosphatidylcholine (EPC). In the most preferred embodiments, the vector-lipid particles are fusogenic particles with enhanced properties in vivo and the noncationic lipid will be DOPE. In other preferred embodiments, the noncationic lipids further comprise polyethylene glycol-based polymers such as PEG 2000, PEG 5000 and polyethylene glycol conjugated to ceramides, as described in co-pending U.S. Ser. No. 08/316, 429, now abandoned.

The amount of noncationic lipid is typically about 2 to about 20 mg of total lipids to 50 μg of vector. Preferably the amount of total lipid is from about 5 to about 10 mg per 50 μg of plasmid.

Following formation of the detergent solution of plasmid-lipid complexes and noncationic lipids, the detergent is removed, preferably by dialysis. The removal of the detergent results in the formation of a lipid-bilayer which surrounds the plasmid providing serum-stable plasmid-lipid particles which have a size of from about 50 nm to about 150 nm. The particles thus formed do not aggregate and have a substantially uniform size.

Alternatively, lipids can be complexed with an AAV vector using a second procedure as follows. The cationic lipids and noncationic lipids are the same as in the first procedure. The selection of an organic solvent typically involves consideration of solvent polarity and the ease with which the solvent can be removed at the later stages of particle formation. The organic solvent, which is also used as a solubilizing agent, is in an amount sufficient to provide a clear single phase mixture of vector and lipids. Suitable solvents include chloroform, dichloromethane, diethylether, cyclohexane, cyclopentane, benzene, toluene, methanol, or other aliphatic alcohols such as propanol, isopropanol, butanol, tert-butanol, iso-butanol, pentanol and hexanol, and combinations thereof.

The vector is contacted with lipids by mixing a first solution of vector, typically aqueous, and a second organic solution of the lipids. Mixing can be accomplished by vortexing. After mixing, the organic solvent is removed by evaporation at reduced pressure of by blowing an insert stream of gas, thus forming an aqueous suspension of serum-stable plasmid-lipid particles. The serum-stable plasmid-lipid particles thus formed are typically from about 50 nm to 150 nm.

Optionally, nonlipid polycations can also be included in the lipid particles. Examples of suitable nonlipid polycations include, hexadimethrine bromide (sold under the brandname "POLYBRENE", from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine and polyethyleneimine.

Other methods, in which DNA is encapsulated in liposomes formed from cationic lipids, such as N-[1-(2,3-dioleyloxy)propyl]-N,N,N-trimethylammonium chloride (DOTMA; Feigner et al., *Proc. Natl. Acad. Sci. USA*, 84, 7413 (1987)), or DOTAP, DDAB, or DOTMA (commercially available under the name "*Lipofectin*)" Hyde et al., *Nature*, 362, 250 (1993)), may also be somewhat effective, if not ideal.

V. Host Cell Range

AAV has a very broad host range, lacks strong species or tissue specificity, and can integrate in virtually any cell type, primary or transformed, of human, simian or rodent origin. Suitable cell types include both proliferating and nonproliferating cells. For example, suitable cell types for use in somatic gene therapy applications include hematopoietic, epithelial, liver, lung, muscle, endothelial, menchymal, neural and bone stem cells, endothelial cells, epithelial cells, myoblasts, hepatocytes, leukocytes, and fibroblasts. Suitable cells for germline gene therapy applications include embryonic stem cells and zygotes. For analysis of expression products in vitro suitable cell lines include HeLa cells, KB cells, JW-2 cells, Detroit 6 cells, COS cells, CV-1 cells, VERO cells, and NIH-3T3 cells. Recipient cells having integrated an AAV vector are stable and are often capable of expressing coding sequences present on the AAV vector indefinitely. If the recipient cells are replicating cells, they are usually capable of expressing coding sequence(s) present on the vector for at least about 10, 20 or 50 cell cycles.

VI. Methods of Gene Therapy (1) Insertion of Functional Copy of a Gene

Some methods of gene therapy serve to compensate for a defect in an endogenous gene by integrating a functional copy of the gene into the host chromosome. The inserted gene replicates with the host DNA and is expressed at a level to compensate for the defective gene. Diseases amendable to treatment by this approach are often characterized by recessive mutations. That is, both copies of an endogenous gene must be defective for symptoms to appear. Such diseases include cystic fibrosis, sickle cell anemia, β-thalassemia, phenylketonuria, galactosemia, Wilson's disease, hemochromatosis, severe combined immunodeficiency disease, alpha-1-antitrypsin deficiency, albinism, alkaptonuria, lysosomal storage diseases, Ehlers-Danlos syndrome, hemophilia, glucose-6-phosphate dehydrogenase deficiency, agammaglobulimenia, diabetes insipidus, Lesch-Nyhan syndrome, muscular dystrophy, Wiskott-Aldrich syndrome, Fabry's disease, and fragile X-syndrome.

There are several methods for introducing an exogenous functional gene to compensate for the above genetic defects. In one approach, cells are removed from a patient suffering from the disease and contacted with a lipid-vector complex in vitro. Cells should be removed from a tissue type in which disease symptoms are manifested. If the cells are capable of replication, and the AAV vector includes a selective marker, cells having integrated and expressed the marker can be selected. Particularly if selection is not performed, it is important that the frequency of integration of AAV into cells be high, for example, at least about 1, 5, 10, 25 or 50% of cells. After integration of the vector into the cellular genome, and optionally, selection, cells are reintroduced into the patient. In this application, and others discussed below (except site-specific recombination to correct dominant mutations), it is not necessary that the gene supplied by the AAV vector be delivered to the same site as is occupied by the defective gene for which it is compensating. However, it is advantageous that the AAV vector preferentially integrate at its specific site in chromosome 19, because it is known that this site of integration does not have any detrimental influence on expression of endogenous genes.

Alternatively, the lipid-vector complex can be introduced directly into a patient as a pharmaceutical composition. The complex is delivered to the tissue(s) affected by the genetic disorder being treated in a therapeutically effective dose. In this and other methods, a therapeutically effective dose is an amount sufficient to cure, or at least partially arrest, the symptoms of the disease and its complications. Effective doses of the compositions of the present invention, for the treatment of the above described conditions will vary depending upon many different factors, including means of administration, target site, physiological state of the patient, and other medicants administered. Thus, treatment dosages will need to be titrated to optimize safety and efficacy. Doses ranging from about 10 ng to 1 g, 100 ng to 100 mg, 1 $\mu$g to 10 mg, or 30–300 $\mu$g DNA per patient are typical. Routes of administration include oral, nasal, gastric, intravenous, intradermal and intramuscular. In in vivo administration, selection is not possible, and a reasonably high frequency of integration, such as is attained by the present methods, is necessary to achieve sufficient expression to compensate for a defective endogenous gene.

The lipid-AAV complexes can also be used to transfect embryonic stem cells or zygotes to achieve germline alterations. See Jaenisch, *Science*, 240, 1468–1474 (1988); Gordon et al. (1984) *Methods Enzymol.* 101, 414; Hogan et al., *Manipulation of the Mouse Embryo: A Laboratory Manual*, C.S.H.L. N.Y. (1986); and Hammer et al. (1985) *Nature* 315, 680; Gandolfi et al. (1987) *J. Reprod. Fert.* 81, 23–28; Rexroad et al. (1988) *J. Anim. Sci.* 66, 947–953 and Eyestone et al. (1989) *J. Reprod. Fert.* 85, 715–720; Camous et al. (1984) *J. Reprod. Fert.* 72, 779–785; Heyman et al. (1987) *Theriogenology* 27, 5968. However, these methods are presently more suitable for veterinary applications that human treatment due to ethical and regulatory constraints in manipulating human embryos.

As an example, cystic fibrosis (CF) is a usually fatal recessive genetic disease, having a high incidence in Caucasian populations. The gene responsible for this disease was isolated by Riordan et al, *Science* 245, 1059–1065 (1989). It encodes a protein called the cystic fibrosis transmembrane conductance regulator (CFTR) which is involved in the transfer of chloride ions ($Cl^-$) through epithelial cell membranes. Mutations in the gene cause defects of $Cl^-$ secretion in epithelial cells leading to the various clinical manifestations. Although CF has a number of symptoms including thickened exocrine gland secretions, pancreatic deficiency, intestinal blockage and malabsorption of fat, the most serious factor affecting mortality is chronic lung disease. Accordingly, to treat a CF patient, an AAV vector containing a coding sequence for a functional CFTR gene product can be complexed with lipid, and optionally, a pharmaceutical excipient and introduced into the patient via nasal administration so that the vector-lipid composition reaches the lungs. The dose of vector-lipid complex is preferably about $10^{10}$ particles. As another example, defects in the α or γ globin genes (see McDonagh & Nienhuis in *Hematology of Infancy and Childhood* (eds. Nathan & Oski, Saunders, Pa., 1992) at pp. 783–879) can be compensated for by ex vivo treatment of hemopoietic stem cells with an AAV-lipid complex containing a functional copy of the gene. The gene integrates into the stem cells which are then reintroduced into the patient. Defects in the gene responsible for Fanconi Anemia Complement Group C can be treated by an analogous strategy (see Walsh et al., *J. Clin. Invest.* 94, 1440–1448 (1994)).

Other applications include the introduction of a functional copy of a tumor suppressor gene into cancerous cell or cells at risk of becoming cancerous. Individuals having defects in one or both copies of an endogenous tumor suppressor gene are particularly at risk of developing cancers. For example, Li-Fraumeni syndrome is a hereditary condition in which individuals receive mutant p53 alleles, resulting in the early onset of various cancers (Harris, *Science* 262, 1980–1981 (1993) Frebourg et al., PNAS 89, 6413–6417 (1992); Malkin et al., *Science* 250, 1233 (1990)). Expression of a tumor suppressor gene in a cancerous cell or a cell at risk of becoming cancerous is effective to prevent, arrest and/or reverse cellular proliferation and other manifestations of the cancerous state. Suitable tumor suppressor genes for use in the invention include p53 (Buchman et al., *Gene* 70, 245–252 (1988)), APC, DCC, Rb, WT1, and NF1 (Marx, *Science* 260, 751–752 (1993); Marshall, *Cell* 64, 313–326 (1991)). Lipid-AAV complexes bearing a functional copy of a tumor suppressor gene are usually administered in vivo by the route most proximal to the intended site of action. For example, skin cancers can be treated by topical administration and leukemia by intravenous administration.

(2) Suppression of Gene Expression

Methods of gene therapy using the AAV-lipid complexes of the invention can also be used for prophylactic or therapeutic treatment of patients or cells, infected with or at risk of being infected with, a pathogenic microorganism, such as HIV. The effectiveness of antisense molecules in blocking target gene functions of impeding virus replication has been demonstrated in a number of different systems (Fried-man et al., *Nature* 335, 452–54 (1988), Malim et al., *Cell* 58, 205–14 (1989) & Trono at al., *Cell* 59, 113–20 (1989)). The AAV vector includes a DNA segment encoding an antisense transcript, which is complementary to a segment of the genome from the pathogenic microorganism. The segment should preferably play an essential role in the lifecycle of the microorganism, and should also be unique to the microorganism (or at least absent from the genome of the natural genome of a patient undergoing therapy). For example, suitable sites for inhibition on the HIV virus includes TAR, REV or nef (Chatterjee et al., *Science* 258, 1485–1488 (1992)). Rev is a regulatory RNA binding protein that facilitates the export of unspliced HIV pre mRNA from the nucleus. Malim et al., *Nature* 338, 254 (1989). Tat is thought to be a transcriptional activator that functions by binding a recognition sequence in 5' flanking mRNA. Karn & Graeble, *Trends Genet.* 8, 365 (1992). The AAV-lipid complex is introduced into leukocytes or hemopoietic stem cells, either ex vivo or by intravenous injection in a therapeutically effective dose. The treatment can be administered prophylactically to HIV⁻ persons, or to persons already infected with HIV.

Analogous methods are used for suppressing expression of endogenous recipient cell genes encoding adhesion proteins. Suppression of adhesion protein expression in useful in aborting undesirable inflammatory responses. Adhesion proteins that can be suppressed by antisense segments present in AAV vectors include integrins, selectins, and immunoglobulin (Ig) superfamily members (see Springer, *Nature* 346, 425–433 (1990). Osborn, *Cell* 62, 3 (1990); Hynes, *Cell* 69, 11 (1992)). Integrins are heterodimeric transmembrane glycoproteins consisting of an a chain (120–180 kDa) and β chain (90–110 kDa), generally having short cytoplasmic domains. The three known integrins, LFA-1, Mac-1 and P150,95, have different alpha subunits, designated CD11a, CD11b and CD11c, and a common beta subunit designated CD18. LFA-1 ($\alpha_L\beta_2$) is expressed on lymphocytes, granulocyte and monocytes, and binds predominantly to an Ig-family member counter-receptor termed ICAM-1 (and perhaps to a lesser extent ICAM-2). ICAM-1 is expressed on many cells, including leukocytes and endothelial cells, and is up-regulated on vascular endothelium by cytokines such as TNF and IL-1. Mac-1 ($\alpha_M\beta_2$) is distributed on neutrophils and monocytes, and also binds to ICAM-1 (and possibly ICAM-2). The third β2 integrin, P150,95 ($\alpha_X\beta_2$), is also found on neutrophils and monocytes. The selectins consist of L-selectin, E-selectin and P-selectin.

VI. Pharmaceutical Compositions

Pharmaceutical compositions comprising the vector-lipid particles of the invention are prepared according to standard techniques and further comprise a pharmaceutically acceptable carrier. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, and globulin. These compositions are usually sterile. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

The concentration of particles in the pharmaceutical formulations can vary widely, i.e., from less than about 0.05%, usually at or at least about 2–5% to as much as 10 to 30% by weight and will be selected primarily by fluid volumes, viscosities, in accordance with the particular mode of administration selected. The amount of particles administered depends upon the particular label used, the disease state being diagnosed and the judgment of the clinician but is generally be between about 0.01 and about 50 mg per kilogram of body weight, preferably between about 0.1 and about 5 mg/kg of body weight.

VII. In Vitro Expression

The AAV-lipid complexes and methods of the invention can also be used for introducing genes into cells in vitro for other purposes besides gene therapy. For example, expression of gene products from an AAV vector in cultured cells is useful for producing large amounts of the gene product. Expression is also useful for general research purposes such as studying expression, genetic complementation or suppression.

EXAMPLES

Figure 3:
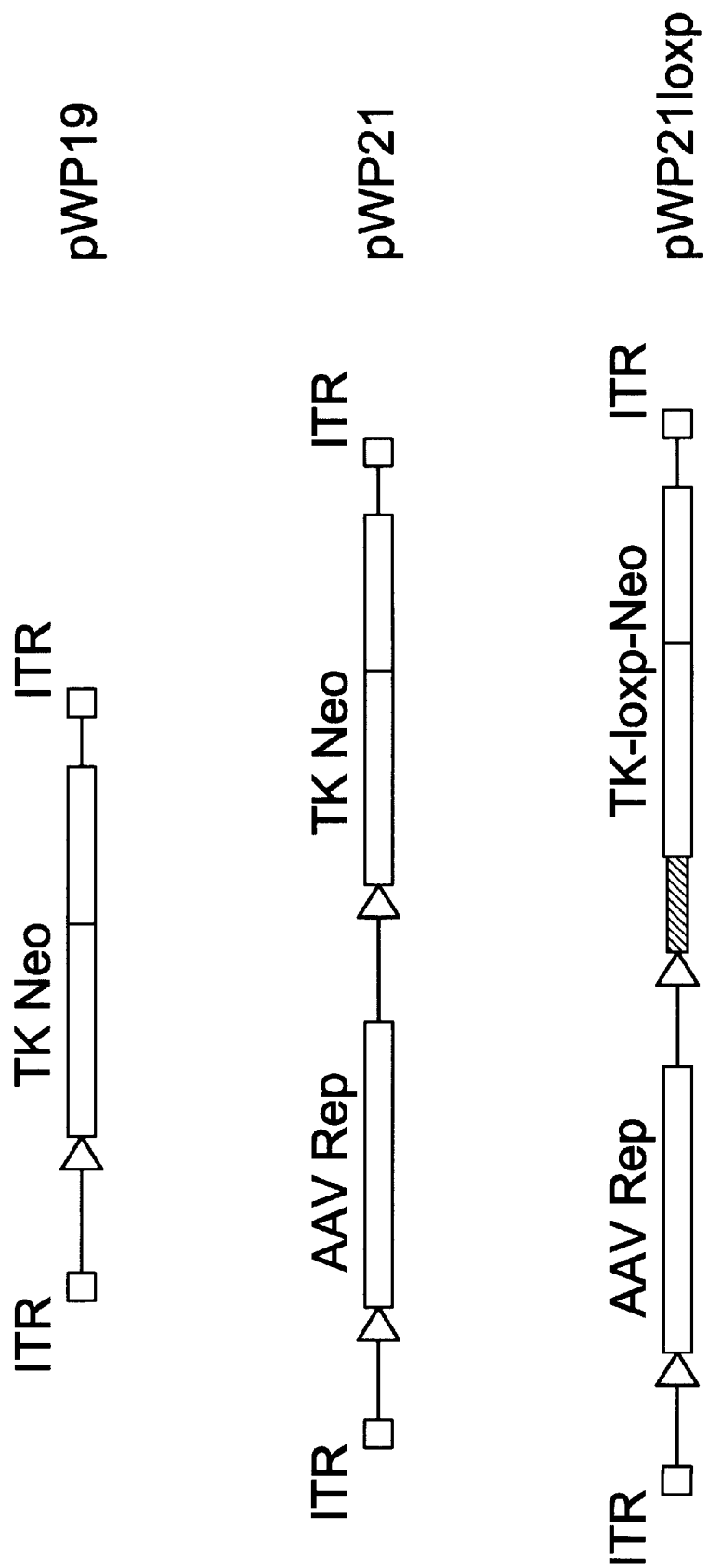
FIG. 3: Maps of adenoassociated virus vectors. The vectors contain two AAV inverted terminal repeats (ITRs) flanking the neo drug resistance marker driven by the thymidine kinase promoter (TK). The plasmid pWP21 also contains the rep gene which directs site specific integration of the AAV vectors onto human chromosome 19 (19q13.4). The loxp integration site was introduced between the TK promoter and the start codon of the neo gene in the plasmid pWP2loxp.

This example tests whether plasmids containing AAV ITRs, a rep gene and an exogenous neo gene (linked to a promoter) can be lipofected into mammalian cells. The two test plasmids were pWP-21 and pWP-19 (FIG. 3). These plasmids are identical except that the rep gene is only present on pWP-21. The rep gene is under the control of its own promoter P5 in pWP-21. pCMVβ (a β-galactosidase expression vector obtained from obtained from Clonetech, Inc.) was also tested as a control.

Two micrograms of plasmid DNA was mixed with 18 pl of the DOPE:DODAC (1:10 reagent) (1 mM total lipids) in a total volume of 200 μl $dH_2O$ in sterile 5 ml polystyrene tubes and incubated at room temperature for 30 min. The transfection mixture was then added to 2.8 ml Dulbecco Modified Eagles Media DMEM before being layered onto $10^3$ adenovirus transformed human embryonic kidney cells (293) (ATCC CRL-1572) maintained in DMEM supplemented with 10% fetal bovine serum in a humidified 5% $CO_2$/95% air incubator. These cells contain adenovirus DNA segments E1-E4 integrated into their genome by transfection of the cells with adenovirus DNA. The transfection mixture was replaced with complete medium after 4 hours. Cells were selected for the presence of Neo marker by the addition of G418 (500 μg/ml) 24 hr after transfection.

Cells were stained with X-gal 24 hr posttransfection. Greater than 90–95% of the cells were stained positive for lacZ expression. This suggested that at these densities, virtually every cell was transfected with the viral constructs.

Neo$^r$ colonies were scored 14 days after transfection by staining live colonies with 0.5% methylene blue. Only cells receiving the AAV plasmids gave rise to substantial numbers of large colonies. The pWP-21 plasmid gave an average of 48 colonies per 1000 transfected cells. pWP-19 produced about 7 colonies per 1000 transfected cells. PCMVβ produced only one G418 resistant colony in four plates of 1000 cells. Comparison of the transfection efficiencies of pWP-19 and pWP-21 reveals that the presence of rep enhances the ability of viral inserts to integrate onto chromosomal sites.

TABLE 1

| Experiment | pWP-21 | pWP-19 | pCMVβ |
|---|---|---|---|
| 1 | 41 | 11 | 0 |
| 2 | 52 | 8 | 1 |
| 3 | 49 | 4 | 0 |
| 4 | 49 | 4 | 0 |
| Frequency | 4.8% | 0.70% | 0.025% |

Frequency of G418 resistant colonies arising from 293 cells transfected with the AAV plasmids pWP-21 and pWP-19 or the control pCMVβ. For each plasmid, four flasks of 1000 cells were plated and transfected with the indicated plasmids. G418 resistant colonies were scored after two weeks of selection.

To determine whether AAV viral inserts had integrated onto the chromosomes, genomic DNA was isolated and digested with BamHI and analyzed by Southern blotting. Genomic DNA was isolated from cell lines by the pronase E/phenol/$CHCl_3$ method. Briefly, a 10 cm dish of cells was washed once with PBS before being lysed with 50 mM Tris HCl pH=7.4, 100 mM NaCl, 1 mM EDTA and 1 mg/ml activated Pronase E. The digestion was allowed to proceed overnight in the humidified $C0_2$ incubator. The lysate was transferred to 15 ml conical tubes and extracted once with phenol/$CHCl_3$. The DNA in the thick lysate was precipitated with 2 volumes of ethanol. The DNA was spooled out using curved pasteur pipettes and dissolved in 100–200 μl TE. These preparations usually give about 100–200 μg of high quality genomic DNA. Southerns were developed by exposing filters to a phosphoimaging screen (Molecular Dynamics) for 4–6 hr and analyzed by phosphoimaging.

Figure 4A:
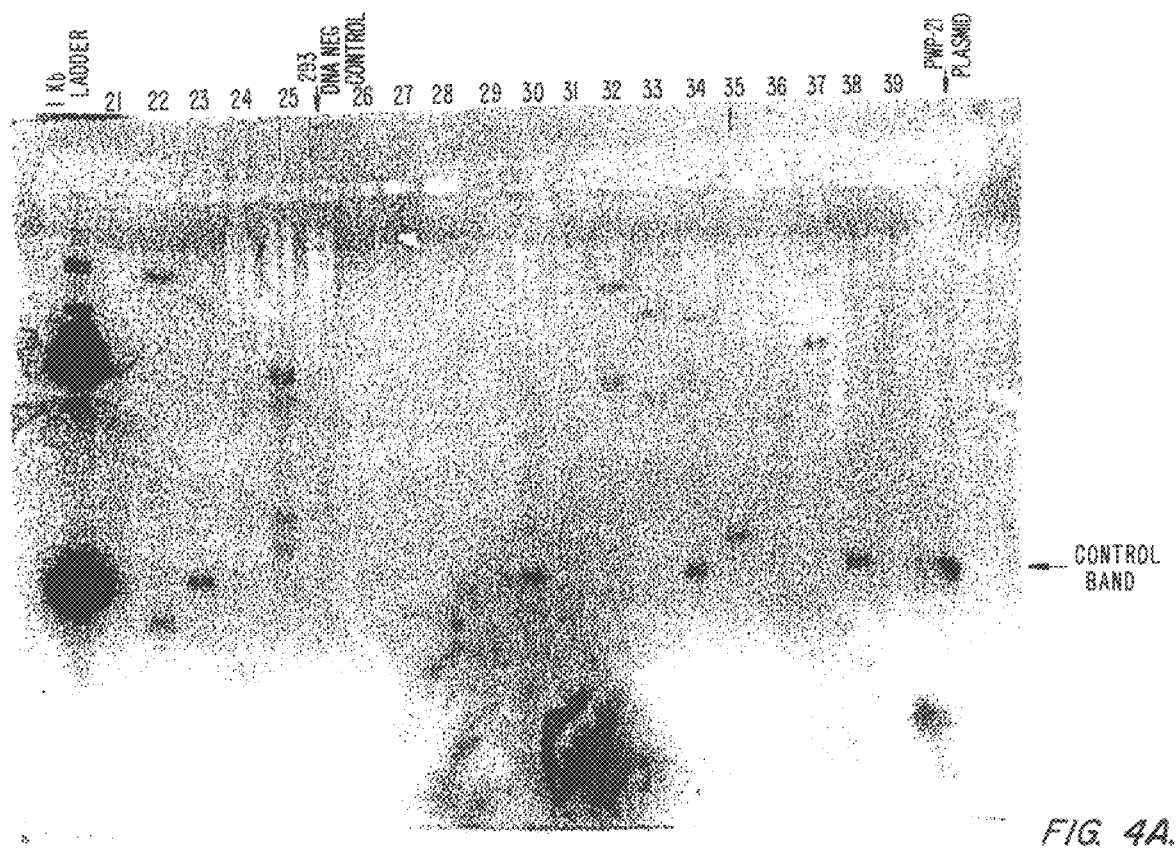
FIG. 4: Southern blot of genomic DNA from cell lines transfected with adeno associated vector.
Figure 4B:
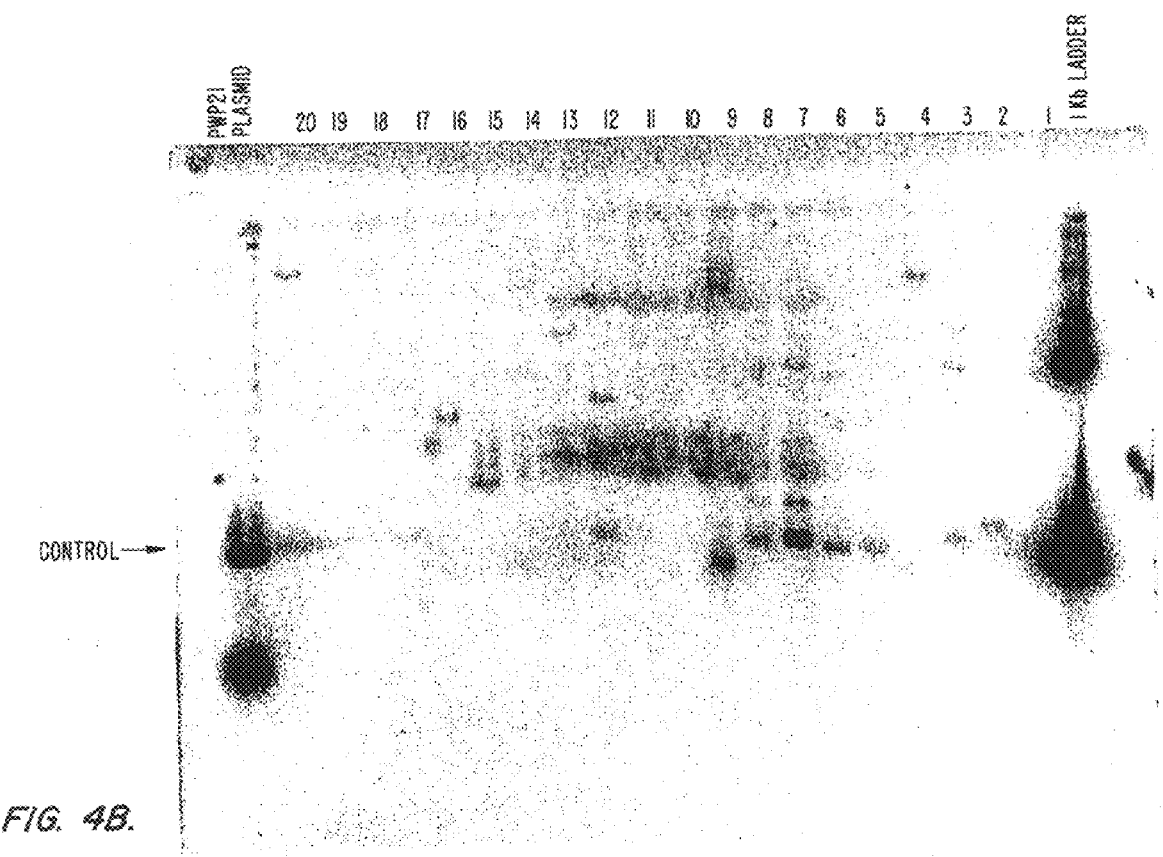

Filters were hybridized with a rep-specific probe to detect viral inserts. The band profiles of most clonal cell lines suggested chrosomomal integration due to the presence of an additional band not present in the intact plasmid (FIG. 4). The additional band was found in a number of cell lines (line 3, 5, 6, 7, 8, 12, 20, 23, 30, 34, and 38).

As a test of the stability of transformed cell lines, clonal G418-resistant cell lines were picked after 21–28 days of selection on G418 and maintained for at least several months in complete medium supplemented with 500 μg/ml. No colonies in the mock-transfected 293 cells survived after 3 weeks of selection.

All publications and patent applications cited above are herein incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

What is claimed is:

1. A serum-stable composition for introducing a nucleic acid fragment into the genome of a cell, comprising:

an expression vector comprising first and second inverted repeated sequences from an adeno associated virus, a rep gene from an adeno associated virus and the nucleic acid fragment; and wherein the expression vector is in a lipid formulation.

2. The composition of claim 1, wherein the expression vector further comprises at least one gene contained within an adenovirus DNA segment wherein said gene is a member selected from the group consisting of E1, E2, E3 and E4.

3. The composition of claim 2, wherein the expression vector comprises said adenovirus DNA segments E1, E2, E3 and E4.

4. The composition of claim 1, wherein the nucleic acid fragment encodes a protein coding sequence in operable linkage to a promoter.

5. The composition of claim 1, wherein the nucleic acid fragment encodes an antisense transcript.

6. The composition of claim 1, wherein the lipid formulation comprises lipids complexed with the vector by a) combining the vector with cationic lipids in a detergent solution to provide a coated vector-lipid complex;

b) contacting noncationic lipids with the coated vector-lipid complex to provide a solution comprising detergent, a vector-lipid complex and noncationic lipids; and c) removing the detergent from the solution of step b to provide a solution of serum-stable plasmid-lipid particles, wherein the plasmid is encapsulated in a lipid bilayer and the particles are serum-stable and have a size from about 50–150 nm.

7. The composition of claim 1, wherein the lipid formulation comprises lipids complexed with the vector by preparing a mixture comprising cationic lipids and non-cationic lipids in an organic solvent;

contacting an aqueous solution of said vector with the mixture to provide a clear single phase and removing the organic solvent to provide a suspension of plasmid-lipid particles, wherein the plasmid is encapsulated in a lipid bilayer, and the particles are stable in serum and have a size of about 50–150 nm.

8. The composition of claim 1, wherein the vector further comprises a loxP site.

9. The composition of claim 1, wherein the vector further comprises a DNA segment encoding a selection marker.

10. The composition of claim 1, wherein the nucleic acid fragment is greater than 5 kb.

11. The composition of claim 1, further comprising a pharmaceutical excipient.

12. The composition of claim 1, wherein the lipid formulation is a lipid complex.

13. The composition of claim 8, further comprising a Cre enzyme or a DNA segment encoding a Cre enzyme.

\* \* \* \* \*